(12) United States Patent
Kaushik et al.

(10) Patent No.: US 8,188,303 B2
(45) Date of Patent: May 29, 2012

(54) **ANTI-MALARIAL COMPOUND ISOLATED FROM *GOMPHOSTEMA NIVEUM***

(75) Inventors: Mahabir Prashad Kaushik, Pradesh (IN); Duraipandian Thavaselvam, Pradesh (IN); Manisha Nivsarkar, Pradesh (IN); Badri Narayan Acharya, Pradesh (IN); Subramaniam Prasanna, Pradesh (IN); Krishnamurthy Sekhar, Pradesh (IN)

(73) Assignee: The Director General, Defence Research and Development Organisation, New Delhi (IN)

( * ) Notice: Subject to any disclaimer, the term of this patent is extended or adjusted under 35 U.S.C. 154(b) by 421 days.

(21) Appl. No.: 11/992,934

(22) PCT Filed: Aug. 30, 2006

(86) PCT No.: PCT/IN2006/000317
§ 371 (c)(1),
(2), (4) Date: Apr. 1, 2010

(87) PCT Pub. No.: WO2007/039915
PCT Pub. Date: Apr. 12, 2007

(65) Prior Publication Data
US 2010/0197781 A1 Aug. 5, 2010

(30) Foreign Application Priority Data
Oct. 4, 2005 (IN) ............................ 2074-DEL-2004

(51) Int. Cl.
*C07D 307/02* (2006.01)
*A01N 43/08* (2006.01)
(52) U.S. Cl. ...................................... 549/479; 514/473
(58) Field of Classification Search .................. 549/479; 514/473
See application file for complete search history.

(56) References Cited

OTHER PUBLICATIONS

He et al. Bioorganic and Medicinal Chemistry Letters, 2010, 20, 1312-1314.*
Zdero, C. "Clerodane Derivatives From Diplostephium." *Phytochemistry* (1992) vol. 31, No. 1, pp. 213-216.
Klayman, D. L. "Qinghaosu (Artemisinin): An Antimalarial Drug from China."*Science, American Association for the Advancement of Science, US* (1985) vol. 228, pp. 1049-1055.
Dutta, M. L., et al. "Ethno-medico botany of the Deories of Assam, India." *Fitoterapia* (1998) vol. LXIX, No. 2, pp. 147-154.
Singh, V. K., et al. "Folk medicines in primary health care: common plants used for the treatment of fevers in India." *Fitoterapia* (1994) vol. LXV, No. 1, pp. 68-74.
Jamir, S. A., et al. "Vascular plan diversity in the sacred groves of Jaintia Hills in northeast India." *Biodiversity and Conservation* (2003) vol. 12, No. 7, pp. 1497-1510.
Singh, K. K., et al. "Role of ethnoherbals in bioprospecting of safe phytomedicines and nutraceuticals for twenty first century." National Seminar on the Frontiers of Research and Development in Medicinal Plan (2000) CIMAP, Lucknow, Abstract No. P-13.
Bhakuni, D. S., et al. "Screening of Indian plans for biological activity: Part XIV." *Indian Journal of Experimental Biology* (1990) vol. 28, No. 7, pp. 619-637.
Rathore, D., et al. "Antimalarial drugs: current status and new developments." *Expert Opinion on Investigational Drugs* (2005) vol. 14, No. 7, pp. 871-883.

* cited by examiner

*Primary Examiner* — Nizal Chandrakumar
(74) *Attorney, Agent, or Firm* — Ladas & Parry LLP

(57) ABSTRACT

The present invention provides an antimalarial compound 3-[2-(2-Hydroxymethyl-1,4a,5-trimethyl-7-oxo-1,2,3,4,4a,7 8,8a-octahydronaphthalen-1-yl)-ethyl]-5H-furan-2-one of the formula 1 given below

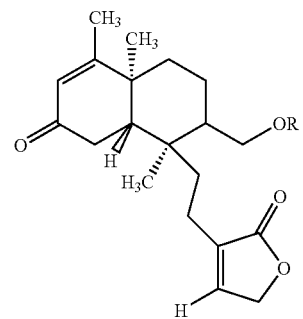

or pharmaceutically acceptable derivatives thereof, isolated from *Gomphostema niveum* and also provides a method for the extraction thereof as well as methods for the treatment of malaria using said compound.

19 Claims, 5 Drawing Sheets

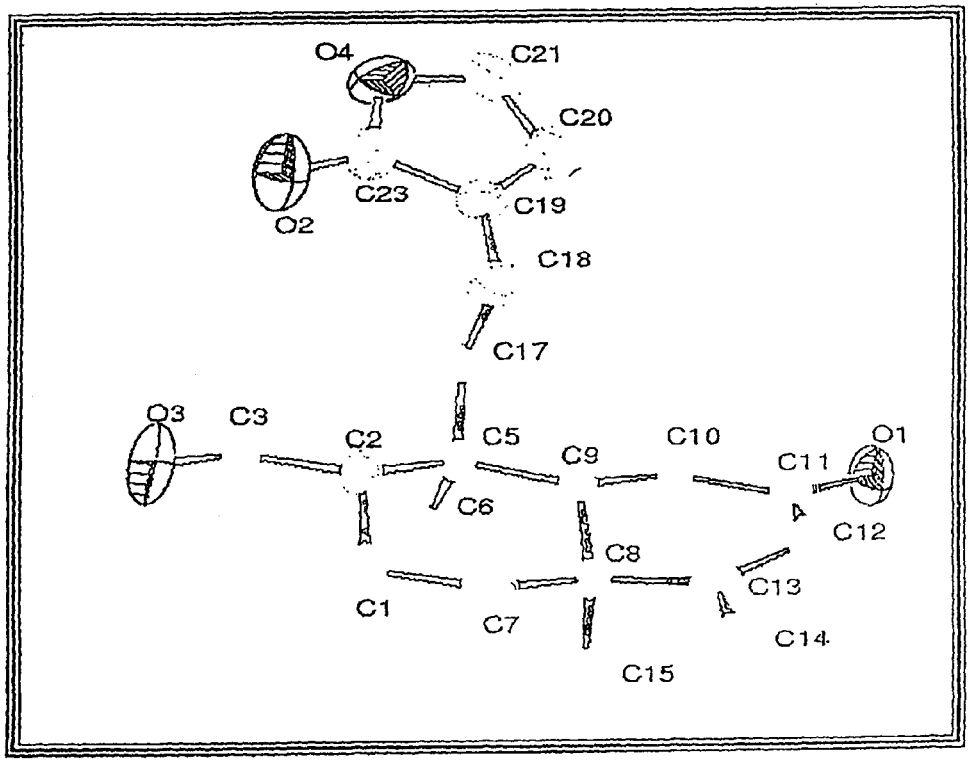
Fig 1. ORTEP diagram of Gomphostinin from X-ray crystallography
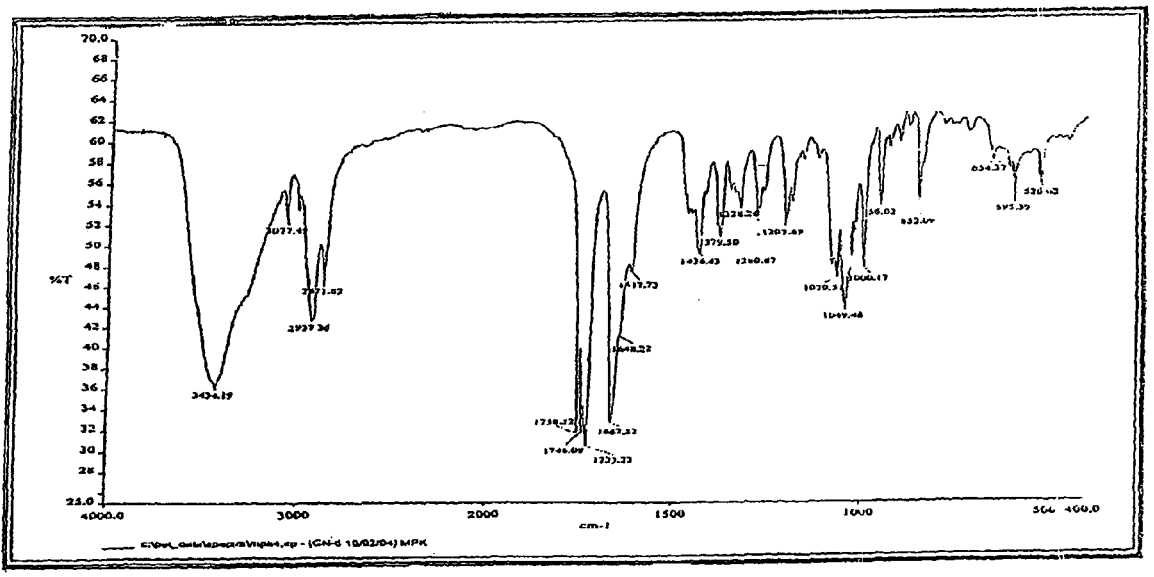
Fig 2. I.R Spectra of Gomphostinin

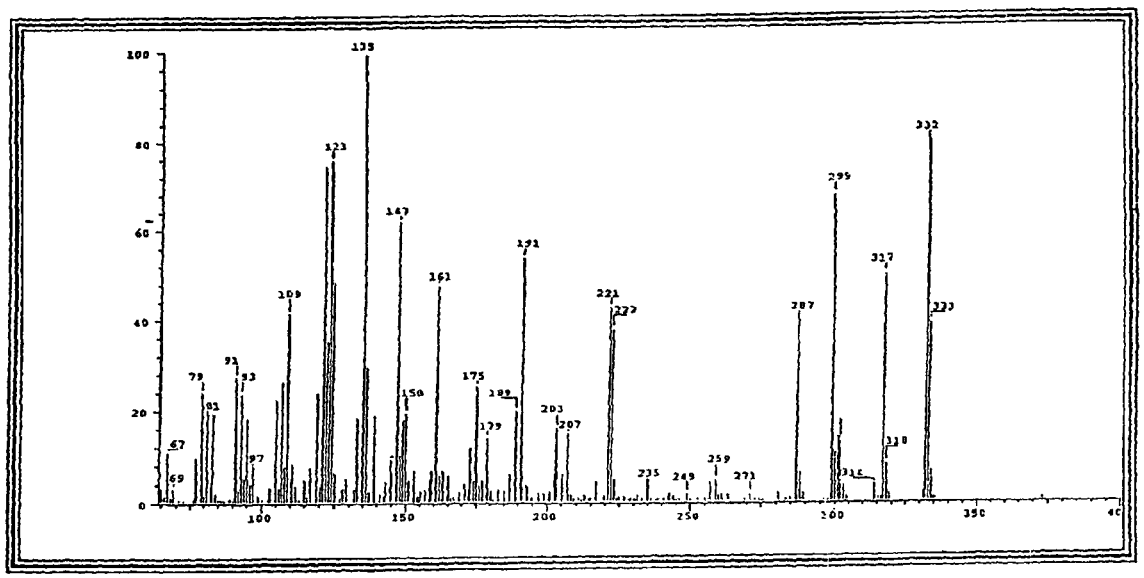
Fig 3. EIMS spectra of Gomphostinin
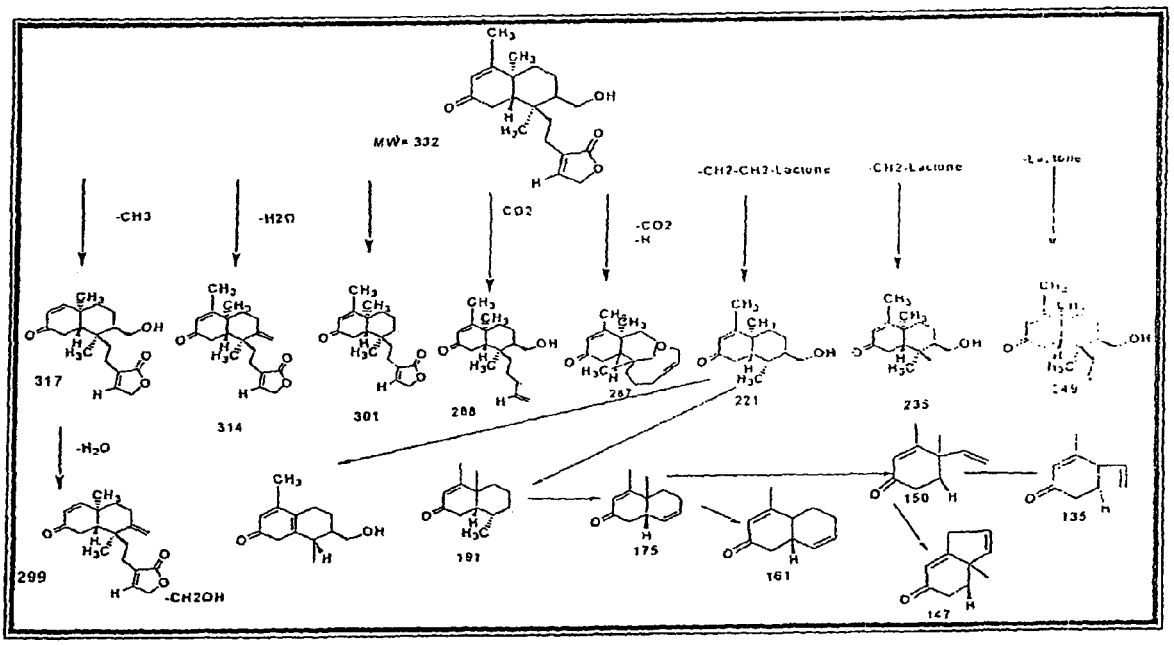
Fig 4. Mass fragmentations of Gomphostinin

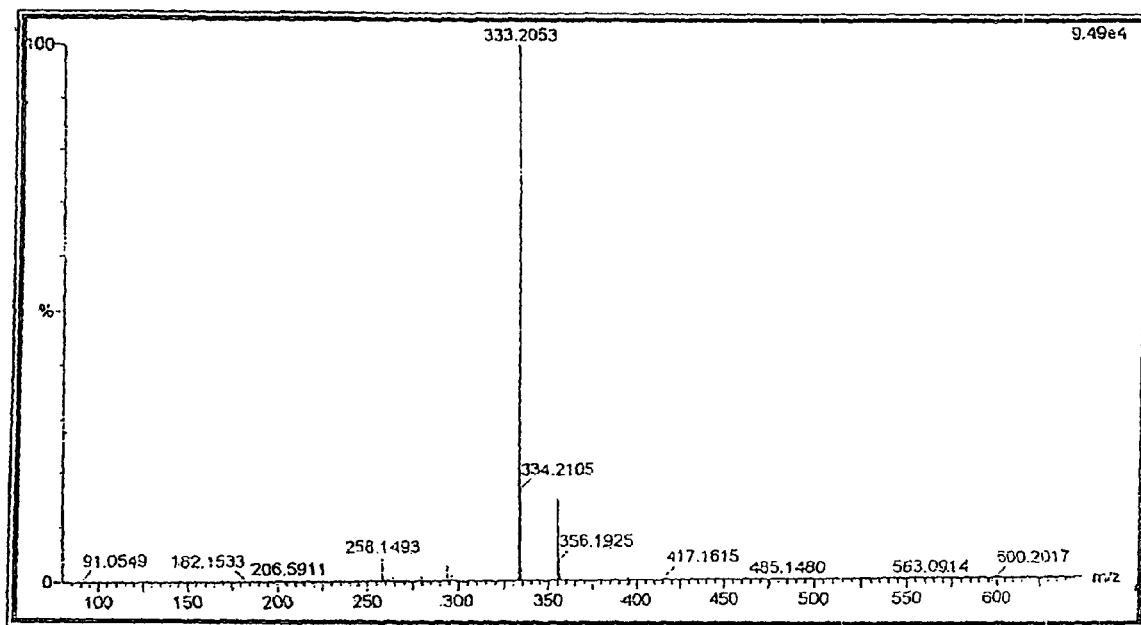
Fig 5. ESI MS spectra of Gomphostinin

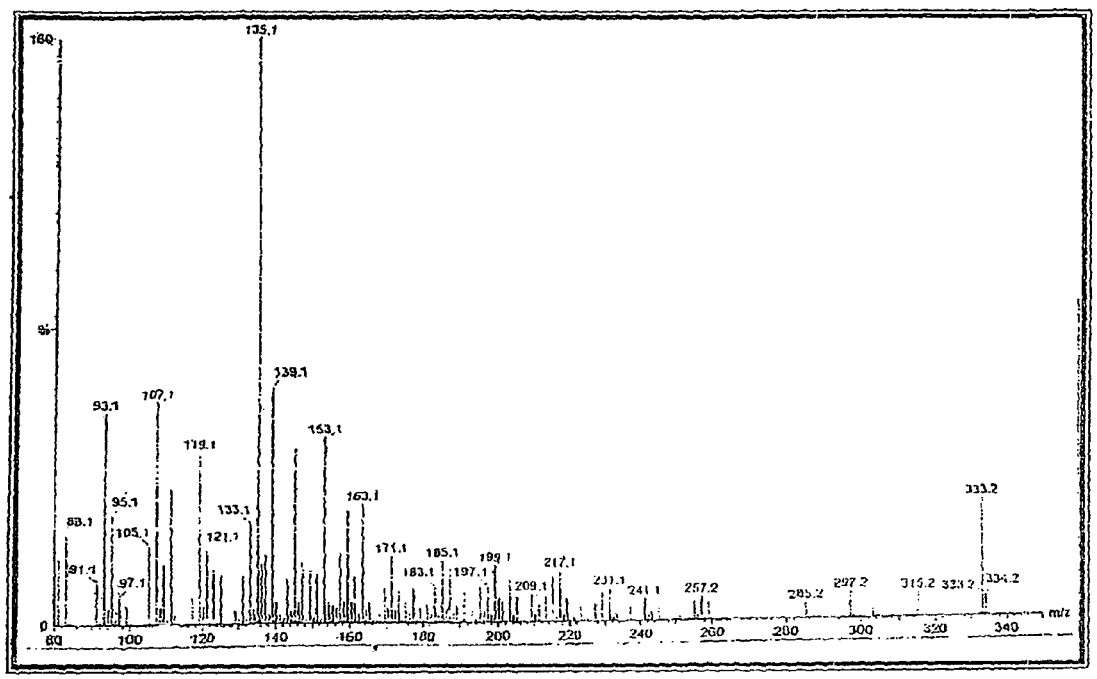
Fig 6. ESI MSMS spectra of Gomphostinin
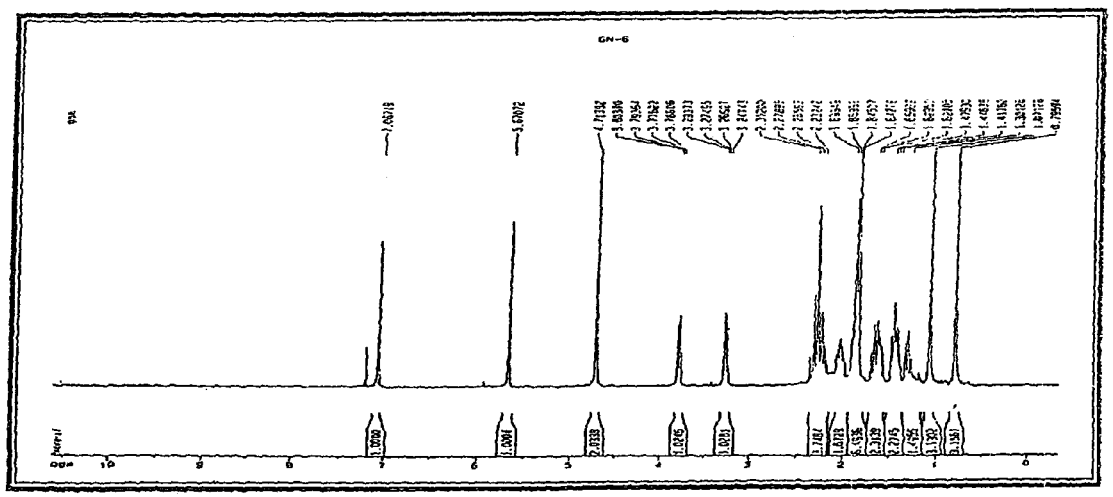
Fig 7. Proton NMR spectra of Gomphostinin

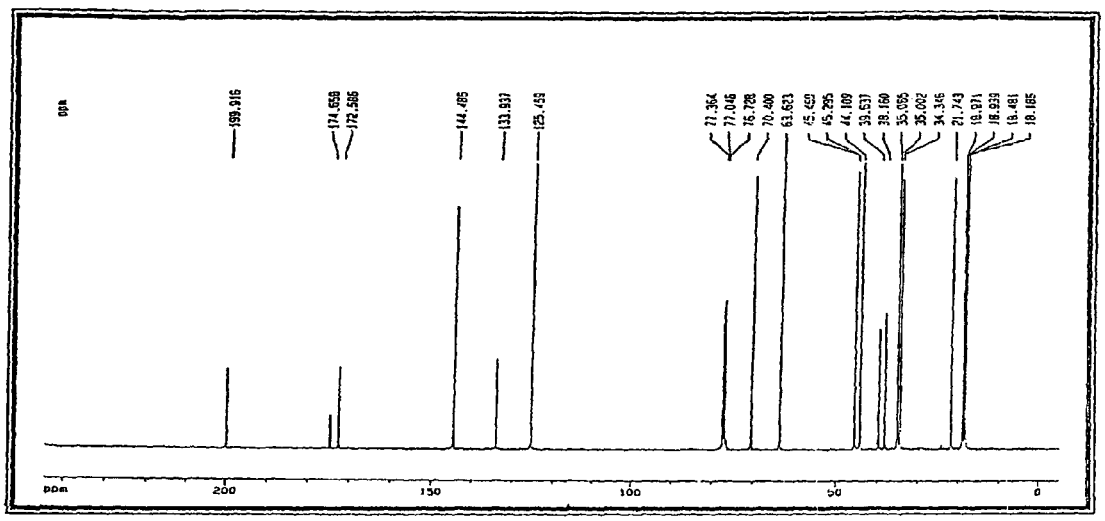
Fig 8. C$^{13}$ NMR spectra of Gomphostinin
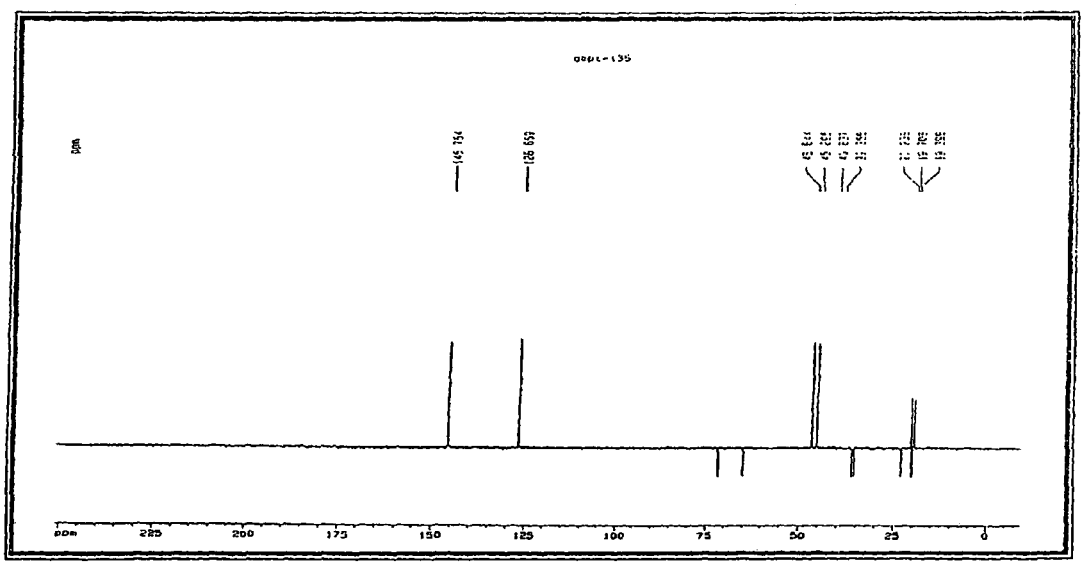
Fig 9. DEPT 135 spectra of Gomphostinin

ANTI-MALARIAL COMPOUND ISOLATED FROM *GOMPHOSTEMA NIVEUM*

FIELD OF INVENTION

The present invention provides a novel anti-malarial compound extracted from *Gomphostema niveum*. The invention relates also to a method for the isolation of such compound and also to its use in the treatment of malaria in subjects suffering from the same. More, specifically, the present invention relates to a method for the inhibition of *Plasmodium faciparum* and *Plasmodium berghi*. The compound of the invention has been extracted and isolated from the extracts of dried leaves of *Gomphostema niveum*.

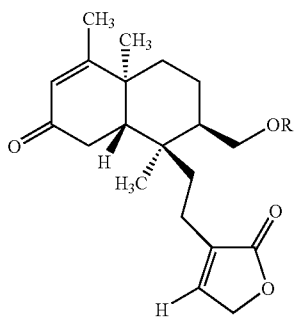

BACKGROUND OF THE INVENTION

Malaria is a disease of epidemic proportions in several parts of the world and is endemic in such areas. In recorded history, malaria leads to more than two million deaths and almost 400 million cases every year in the tropical and subtropical regions of the world (Greenwood et. al Nature (415), 670(2002)). Malaria is a parasitic infection. Of the various forms of malaria that occur, cerebral malaria caused by *Plasmodium falciparum*, is a significant cause for mortality. Over half of the world population lives in areas where they are susceptible to malarial infection (Sachs et. al, Nature, (415, 686 (2002).

While several drugs are known to be anti-malarial and while governments over the world are taking steps to eliminate the disease by vector control methods, the incidence of malaria has worsened over the past few years. This is primarily due to malarial parasites becoming increasingly resistant to several anti-malarial drugs (Reed et. al, Nature (403), 906 (2000)) commercially available like chloroquine (Ringwaid et. al, *Bulletin of the world health organization*, 77(1), 34, (1999)). Elimination of malaria as a pandemic disease using vector control method such as use of insecticides are rendered more complex due to the parallel spread of resistance in the mosquito vector to currently available insecticides.

Most anti-malarial drugs such as chloroquine, mefloquine, primaquine etc. are product of chemical synthesis. However, over the past few years a significant amount of effort is being made to screen natural resources to obtain new classes of compounds/mixtures which can be used as anti-malarials. Such efforts have led, for example, to the discovery of artemisinin from the Chinese plant *Artemisia annua* as a potential anti-malarial. The development of resistance in the parasite to existing compounds as well as the vector's resistance to insecticides has resulted in an ongoing and urgent need to identify new classes of anti-malarials and develop them as drugs with varied model of action to overcome the problem of resistance (Tulp et al, *Drug discovery today* (9) 450, (2004)).

Prior art has focused on the use of plant sources to obtain anti-malarial drugs. For example, the discovery of quinine (Brooking, GB 106430, (1917)) and artemisinin (Klayman, Science (228), 1049 (1985)) hitherto extremely potent anti-malarial drugs, both from plant sources, has lead to the study of plants as anti-malarial agents. The ethanopharmacological approach for the search of new anti-malarial agents from the plant sources has proved to be more predictive. Several research groups are now working to develop new active compounds as an alternative to chloroquine and artether, a derivative of artemisinin. Plants may well prove to be the source of new anti-malarial drugs in view of the success with the two important chemotherapeutic agents, quinine and artemisinin, both of which are derived from plants. Plants in addition to Cichona that have been used against fever and malaria include *Dichroa febrifuga*, which grows in China. However, being alkaloidal in nature febrigugine and isofibrifugine have been reported to be highly toxic for use in humans (Jiang et. al WO2004000319, (2003)). Recently again in China a naturally derived anti-malarial compound *Qinghaoso* has been investigated. Recently Ihara et. al disclosed about compounds having anti-malarial activity (U.S. Pat. No. 6,710,074 (2004)) from synthesis. There are several patent documents and published patent applications which disclose different classes of compounds with anti-malarial activity, for example, substitute 1,2,4 trioxane (U.S. Pat. No. 6,737,438 (2004)), flavonoids (WO2004000306 (2003)). Napthylisoquinoline (U.S. Pat. No. 6,627,641 (2003)), indoloquinazoles (U.S. Pat. No. 6,531,487 (2003)), trioxolanes (U.S. Pat. No. 6,486,199 (2002)), betacarboline alkaloids (U.S. Pat. No. 6,143,756 (2000)), vocamine (WO9948501 (1999)), acetyl glucosamine derivatives (DE3220426 (1983) and so on. U.S. Pat. No. 6,710,074, WO2004000319, U.S. Pat. No. 5,362,726, US2003212098, WO2004000306, EP1076057, WO9948501, U.S. Pat. No. 4,290,553, U.S. Pat. No. 6,143,756 and U.S. Pat. No. 6,627,641 disclose compound having anti-*Plasmodium falciparum* activity with a natural origin, mainly plaints. Natural resources will be the potential sources for future drug development against malaria.

OBJECTS OF THE PRESENT INVENTION

The main object of the invention is to provide a novel active principle of natural origin which has use as an anti-malarial.

It is another object of the invention to provide a method for the extraction of a novel anti-malarial compound from *Gomphostema niveum*.

It is a further object to provide a method for the treatment/inhibition of malaria based on *P. falciparum* or *P. berghi* using a compound of natural origin.

STATEMENT OF THE INVENTION

The present invention proposed a novel anti-malarial compound, which has been extracted, isolated, chemically identified from the leave of *Gomphostema niveum*, a plant available in North East India, and named as Gomphostinin. The compound Gomphostinin is a γ-lactone and the structure given below.

Accordingly, the present invention provides a novel anti-malarial compound namely, 3-[2-(2-Hydroxymethyl-1,4a,5-trimethyl-7-oxo-1,2,3,4,4a,7 8,8a-octahydronaphthalen-1-yl)-ethyl]-5H-furan-2-one of the formula 1 given below extracted from *Gomphostema niveum* and pharmaceutically acceptable derivatives thereof.

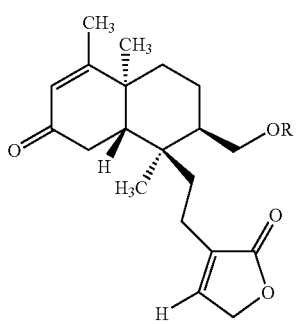

The present invention also provides a method for the preparation of substantially purified compound in Claim 1 from the leaves, barks, roots of *G. niveum*, comprising:
(a) subjecting dried and powdered plant parts of *Gomphostema niveum* to extraction with a solvent;
(b) filtering the extract obtained in step (a) and evaporating the extract under reduced pressure;
(c) lyophilizing the filtrate obtained in step (b) to obtain a powder form;
(d) isolating compound of formula 1 from the powder.

In one embodiment of the invention, the compound is isolated from the dried bark, roots or leaves of *Gomphostema niveum*.

In another embodiment of the invention, the plant parts are air dried and then pulverized in a conventional manner to obtain the powder.

In another embodiment of the invention, the solvent is selected from the group consisting of water, methanol, ethanol, chloroform, diethyl ether and any mixture thereof.

In another embodiment of the invention, the solvent is selected from the group consisting of a mixture of water and methanol, mixture of ethanol and water, mixture of chloroform and a mixture of ethanol, methanol, chloroform and diethyl ether.

In another embodiment of the invention, the compound is isolated from the plant extract by normal phase thin layer chromatography and column chromatography, or by reversed phase thin layer chromatography and column chromatography.

The present invention also provides a pharmaceutical composition for the treatment of malaria comprising a pharmaceutically acceptable amount of a compound of formula 1 or a pharmaceutically acceptable derivative thereof

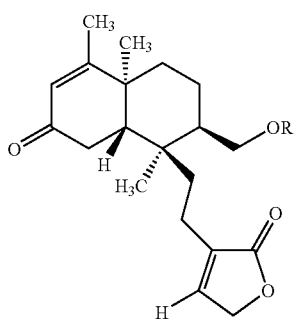

and one or more pharmaceutically acceptable additives.
In one embodiment of the invention, the one or more pharmaceutically acceptable additives are selected from the group consisting of adjuvants, carriers, excipients, diluents, flavoring agents, emulsifiers, viscosity enhancers, binder, stabilizers, solvents and the like.

The present invention also provides a method for the treatment of malaria in a subject suffering from the same comprising administering to said subject a pharmaceutical composition comprising pharmaceutically acceptable amount of a compound of formula 1

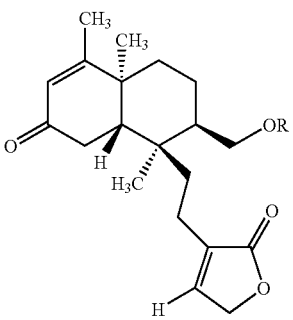

and one or more pharmaceutically acceptable additives.
The malaria being treated could be malaria caused by *P. falciparum* or *P. berghi*.

The compound of formula 1 or pharmaceutical composition containing said compound can be administered orally.

Additional objects, features and advantage of the present invention will become apparent to those skilled in the art from the following detailed description of preferred embodiments exemplifying the best mode of carrying out the invention.

BRIEF DESCRIPTION OF THE ACCOMPANYING DRAWINGS

FIG. 1 is the ORTEP diagram of 3-[2-(2-Hydroxymethyl-1,4a,5-trimethyl-7-oxo-1,2,3,4,4a,7 8,8a-octahydronaphthalen-1-yl)-ethyl]-5H-furan-2-one of the formula 1 being the compound of the invention.

FIG. 2 is the IR spectra of the compound of formula 1.
FIG. 3 is the EIMS spectra of the compound of formula 1.
FIG. 4 is the mass fragmentation data of compound of formula 1.
FIG. 5 is the ESI MS spectra of the compound of formula 1.
FIG. 6 is the ESI MSMS spectra of the compound of formula 1.
FIG. 7 is the proton NMR spectra of the compound of formula 1.
FIG. 8 is the $C^{13}$ NMR of compound of formula 1.
FIG. 9 is the DEPT 135 spectra of the compound of formula 1.

DETAILED DESCRIPTION OF THE INVENTION

Malaria is a significant parasitic infection for humans due to its high morbidity and mortality a threat to over 2 billion people living in areas of high incidence. *P. faciparum*, the causative agent of the malignant form of malaria, has high adaptability by mutation and is resistant to various types of anti-malarial drug, a serious setback to anti-malarial programs since it precludes the use of cheap and previously effective drugs like chloroquine. New families of active compounds are needed as well as poly chemotherapy associating molecules with independent mechanism of action in order to decrease the risk of resistance.

The success of the anti-malarial drug quinine and the discovery of artemisinin, the most potent anti-malarial drug both from plant sources have lead to the study of plants as anti-malarial agent. The aqueous extract of dried powdered leaves of G. niveum shows anti-malarial activity. Use of crude extract for the treatment of malaria may not be efficient and reliant. It has also the significant disadvantage of culturing the North Eastern Indian plant, rather than the utilization of an isolated pure and active component. Hence the need is to isolate and identify the active component present in the crude extract of G. niveum.

Gomphostinin and its derivatives are anti-malarial compounds having the ability to inhibit the growth of malaria parasites. Gomphostinin and its derivatives are showing significant inhibitory activity against P. falciparum in-vitro and P. berghi in-vivo. The compound is preferably administered orally. The bioactive compounds can also be administered to the patient in combination with pharmaceutically additives like carrier's diluents, solvents, filter, lubricant, excipient binder or stabilizer.

From preliminary screening it has observed that aqueous leaf extract of G. niveum has anti-malarial activity. However the component or components responsible for anti-malarial activity is unknown. In view of the evidence of anti-malarial activity of leaf extract, the present inventors purified and identified the responsible compound. Using bio-guided fractionation and chromatographic techniques, a white crystalline compound was isolated and purified from aqueous extract of dried leaves of G. niveum showing inhibition effect against P. falciparum in-vitro and P. bergei in-vivo. The structure of Gomphostinin shows it to be a novel compound. The IUPAC nomenclature of the compound would be 3-[2-(2-Hydroxymethyl-1,4a,5-trimethyl-7-oxo-1, 2, 3, 4, 4a,7 8,8a-octanhydronaphthalen-1-yl)-ethyl]-5H-furan-2-one. The mechanism by which Gomphostinin exhibits its anti-malarial activity has not been elucidated yet. However, it has been demonstrated that Gomphostinin is effective in vitro against P. falciparum and P. bergei malaria parasites. Gomphostinin offers another approach to the prevention and treatment of malaria, which is sorely needed in view of the resistance of P. falciparum to multiple known anti-malarial drugs.

The active fraction is extracted from dried plant parts such as leaves, bark and roots of *Gomphostema niveum*, preferably air dried leaves. The solvent used for extraction can be any one or more of water, methanol, ethanol, chloroform or diethyl ether. The active compound is isolated from the plant extracts by normal phase thin layer chromatography and column chromatography or by reverse phase thin layer chromatography and column chromatography. In the method of the invention, the active compound was analyzed by normal phase high performance liquid column chromatography and also by reversed phase high performance liquid chromatography. The isolated active compound was recrystallized and the structure determined by X-ray crystallography as well as by spectroscopy. After recrystallization, the efficacy of the compound was tested against malaria parasites *Plasmodium falciparum* in-vitro and plasmodium *bergei* in-vivo, particularly in comparison with chloroquine phosphate.

Example 1

Extraction of Gomphostinin

G. niveum leaves are collected in the month of June & September from Dhimaji, Assam located in the North Eastern Part of India. Powdered air dried leaves of G. niveum (100 gm) are extracted with water 1000 ml in refluxed condition for 6 hours. The concentrated extract is partioned with 200 ml diethyl ether thrice. The diethyl ether portions are mixed and concentrated to dryness (B) under reduced pressure.

Example 2

Isolation of Gomphostinin

About 10 g of B is packed on to a silica gel column and eluted in hexane-ethyl acetate system. The column fractions are subsequently analyzed for their inhibitory activity against P. falciparum and P. Bergei. Another of solvents used for the elution of different components from the ether fraction are hexane 500 ml (1-8 fractions), 10% ethylacetate in hexane (1 lit), 40% ethylacetate in hexane (1 lit) 50% ethylacetate in hexane (1.5 lit). The result indicated that the compound in column fractions eluted using 50% hexane in ethyl acetate is able to inhibit the malarial parasites and therefore possess the ability to cure malaria. Gomphostenin is obtained as white crystalline substance from above column fraction on drying and re-crystallizing from diethyl ether.

Example 3

High Performance Liquid Chromatographic (HPLC) Analysis

An HPLC method is developed for rapid evaluation of extraction and isolation processes by using water, acetonitrile in the ratio 60:40 as mobile phase at a flow rate of 1 ml per minute. An SGE Nucleosil C8 (250*4.6, 5 u) column is used and UV detector wavelength is set at 254 nm. One mg of the compound is dissolved in one ml of methanol and 5 µl of the solution is injected to the HPLC system. Peak appears at 5.6 min is due to Gomphostinin.

Example 4

Re-Crystallization of Gomphostinin

After isolation by column chromatography and ensuring purity by HPLC analysis, 50 mg of the compound is dissolved in 2 ml of diethyl ether. The solution is left standing overnight in a test tube to enable slow evaporation of diethyl ether. Fine crystals are appeared which are taken for X-ray crystallography.

Example 5

X-Ray Crystallography

A small crystal is picked from the bottom of the test tube and put in the probe of X-ray crystallography. Chemical structure of the compound was determined by X-ray crystallography. The x-ray crystallographic structure (FIG. 1) indicates the presence of a five number γ-lactone ring. The IUPAC nomenclature of the compound will be 3-[2-(2-Hydroxymethyl-1,4a,5-trimethyl-7-oxo-1, 2, 3, 4, 4a,7,8,8a-octahydronaphthalen-1-yl)-ethyl]-5H-furan-2-one.

Example 6

Spectroscopic Analysis

Infrared (IR) spectrum (FIG. 2) of Gomphostinin recorded in KBr pellet displayed strong carbonyl absorptions at 1667 and 1733 $cm^{-1}$ and strong OH stretching absorption at 3434 $cm^{-1}$. Absorptions at 1733 and 1759 $cm^{-1}$ are characteristic to lactones where as absorption at 1667 cm-1 is due to a carbonyl group which is not in conjugation with the lactone.

An electron ionization (EI) mass spectrum (FIG. 3) of Gomphostinin is acquired using a Finnigan MAT mass spectrometer. The EI mass spectra of gomphostenin gave an $M^+$ ion at m/z 332 and fragment ions at m/z 317, 299, 287, 222, 221, 191, 175, 161, 150, 147, and 135 (FIG. 4). Electro spray ionization mass (ESI-MS) spectrometry is carried out using a quadrapole time of flight (Q ToF Micro) mass spectrometer of Micromass. The compound is injected to the mass spectrometer using Waters HPLC system and ESI+ is used as ionization mode. ESI-MS spectrum of gomphostinin gave an $(M+H)^+$ ion at m/z 333 (FIG. 5). The high resolution mass (HRMS) measurement (FIG. 6) of ion at 333 Da is carried out by Q-ToF micro mass spectrometer using lock spray reference mass sulfadimethoxine (311.0814 Da), keeping collision energy at 25 V, sample cone voltage at 40V, argon as collision gas. The measured exact mass 333.2053 corresponds to an empirical formula $C_{20}H_{28}O_4$ with an error of 1.3 mDa units.

The proton NMR spectrum (FIG. 7) of Gomphostenin gave resonances corresponding to 28 protons. The spectrum contains signals due to three methyl groups at 0.80, 1.05 and 1.89 ppm. Methyl group having signal 1.89 ppm is attached to a $sp^2$ hybridized carbon i.e. C=C. The full proton-decoupled carbon NMR spectrum (FIG. 8) of Gomphostenin indicates the presence of twenty carbons. DEPT 135 analysis (FIG. 9) in combination with carbon NMR indicates the presence of three methyl, seven methylene, four methyne and six quaternary carbons. Signal at 199 ppm is due to a carbonyl group present in conjugation with a carbon double bond. Signal at 174 ppm indicates the presence of a carbonyl group of a lactone which is detected in infrared studies. Signals at 172, 144, 133 and 125 ppms indicate the presence of two carbon-carbon double bonds. Signal at 133 ppm is a quaternary carbon. Hence the methyl group having proton NMR shift at 1.89 ppm is attached to this carbon. The number of carbon and hydrogen obtained from NMR studies are matching with the empirical formula calculated from mass spectrometric studies.

Example 7

In-Vitro Evaluation of Anti-Malarial Activity

Two strains of chloroquine sensitive strain and one strain of *P. falciparum* isolated from patients from Jagadalpur region of India and maintained in vitro. The cultures are maintained as per the standard culture procedures.

The parasites are growth in O +ve human RBCs with the addition of RPMI 1640 culture media with 10% Human serum as supplement. The cells are incubated at 37° C. at 5% $CO_2$ atmosphere and the parasitemia is checked after 24 hrs and media changed. When parasitemia exceeded 10% parasitized cells the culture is subcultured with the addition of fresh RBC. The parasite growth is synchronized by the sorbitol lysis method and synchronized ring stage parasites are used for testing. The in-vitro testing is done in 100 µl complete media per well with the addition of 10 µl of erythrocytes with 2% of ring stages of parasites. All the tests are run in duplicates with in 96 well flat bottomed tissue culture plate and double dilutions are made for each of the test compound with individual control wells only with the RPMI 1640 and human serum supplement. The growth of the parasites in the presence of each of the test compound, chloroquine and control wells are monitored by the examination of the giemsa stained blood smears made after 24 hrs of incubation. The counting is done for the presence of mature schizsonts among 200 asexual parasites and the average schizont maturation inhibition is calculated by the formula $(1-N_t/N_c)\times 100$ where in $N_t$ and $N_c$ represent the number of schizont present in the test and control respectively. The IC 50 and IC 90 values are calculated by using the commercial statistical package Sigmastat.

Gomhostinin was analyzed to determine the $IC_{50}$ value, the median concentration of the compound which effectively inhibits the growth of 50% of the test organism exposed to it within a stated period of time. As controls $IC_{50}$ chloroquine and artether were also determined. The results are shown in Table 1.

|  | $IC_{50}$ in µg/ml | $IC_{90}$ in µg/ml |
| --- | --- | --- |
| Crude extract | 153.23 | 752.29 |
| Gomphostenin | 8.23 | 24.29 |
| Chloroquine | 12.87 | 23.69 |

We claim:

1. 3-[2-(2-Hydroxymethyl-1,4-a,5-trimethyl-7-oxo-1,2,3, 4,4a,7 8,8a-octahydronaphthalen-1-yl)-ethyl]-5H-furan-2-one of formula 1 given below

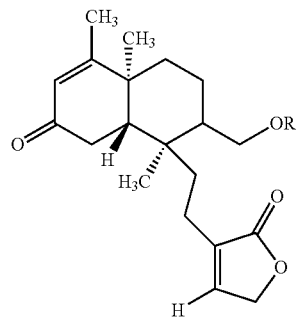

wherein R represents hydrogen.

2. A method of preparing substantially purified compound of claim 1 from the leaves, barks, roots of *Gomphostema niveum*, comprising:
(a) subjecting dried and powdered plant parts of *Gomphostema niveum* to extraction with a solvent;
(b) filtering the extract obtained in step (a) and evaporating the extract under reduced pressure;
(c) lyophilizing the filtrate obtained in step (b) to obtain a powder form; and
(d) isolating compound of formula 1 from the powder

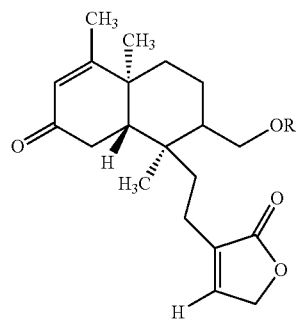

wherein R represents hydrogen.

3. The method as claimed in claim 2, wherein the compound is isolated from the dried leaves of *Gomphostema niveum*.

4. The method as claimed in claim 2, wherein the solvent is selected from the group consisting of water, methanol, ethanol, chloroform, diethyl ether and any mixture thereof.

5. The method as claimed in claim 4, wherein the solvent is water.

6. The method as claimed in claim 4, wherein the solvent is methanol.

7. The method as claimed in claim 4, wherein the solvent is ethanol.

8. The method as claimed in claim 4, wherein the solvent is a mixture of water and methanol.

9. The method as claimed in claim 4, wherein the solvent is a mixture of ethanol and water.

10. The method as claimed in claim 4, wherein the solvent is a mixture of methanol and chloroform.

11. The method as claimed in claim 4, wherein the solvent is a mixture of ethanol and chloroform.

12. The method as claimed in claim 4, wherein the solvent is chloroform.

13. The method as claimed in claim 4, wherein the solvent is mixture of diethyl ether and chloroform.

14. The method as claimed in claim 4, wherein the solvent is mixture of ethanol, methanol, chloroform and diethyl ether.

15. The method as claimed in claim 2, wherein the compound is isolated from the plant extract by normal phase thin layer chromatography and column chromatography, or by reverse phase thin layer chromatography and column chromatography.

16. The method as claimed in claim 2, wherein the plant parts are selected from the group consisting of leaves, roots and bark.

17. The method as claimed in claim 2, wherein the plant parts are air dried and then pulverized in a conventional manner to obtain the powder.

18. A pharmaceutical composition for the treatment of malaria comprising a pharmaceutically acceptable amount of a compound of formula 1

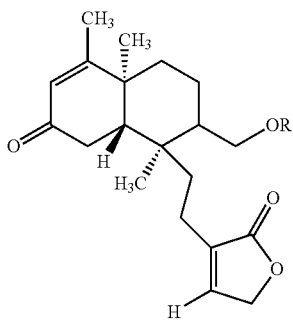

where R represents hydrogen, and one or more pharmaceutically acceptable additives.

19. The composition as claimed in claim 18, wherein said one or more pharmaceutically acceptable additives are selected from the group consisting of adjuvants, carriers, excipients, diluents, flavoring agents, emulsifiers, viscosity enhancers, binders, stabilizers, and solvents or a mixture thereof.

\* \* \* \* \*